United States Patent [19]

Rzeszotarski et al.

[11] Patent Number: 4,877,779
[45] Date of Patent: Oct. 31, 1989

[54] 2-AMINOMETHYLALKYNYLALKYL-1,3-DITHIANE DERIVATIVES

[75] Inventors: Waclaw J. Rzeszotarski, Millersville; Maria E. Guzewska, Pasadena; John P. Carter, Baltimore; Theodore C. Adams, Perry Hall; Andrea C. Dupont, Lutherville; Carl Kaiser, Millersville, all of Md.

[73] Assignee: Marion Laboratories, Inc., Kansas City, Mo.

[21] Appl. No.: 194,903

[22] Filed: May 17, 1988

[51] Int. Cl.$^4$ .............. A61K 31/385; A61K 31/535; C07D 405/12; C07D 339/08
[52] U.S. Cl. ............................ 514/63; 514/227.8; 514/231.5; 514/252; 514/326; 514/422; 514/436; 544/60; 544/69; 544/145; 544/229; 544/374; 546/14; 546/207; 548/406; 548/527; 549/4; 549/22
[58] Field of Search .............. 549/4, 22; 546/14, 207; 544/60, 69, 145, 229, 374; 514/63, 227.8, 231.5, 252, 326, 422, 436; 548/406, 527

[56] References Cited

U.S. PATENT DOCUMENTS 3,086,021  4/1963  Biel ........................................ 548/527

Primary Examiner—Mary C. Lee
Assistant Examiner—Mary Sue Howard
Attorney, Agent, or Firm—Theresa M. Gillis

[57] ABSTRACT

Novel compounds and their salts are disclosed having the Formulas:

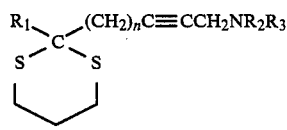

-continued
and

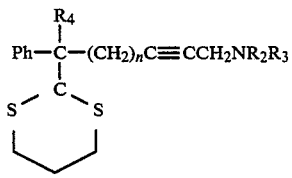

wherein:
$R_1$ is hydrogen, phenyl, 9H-fluoren-9-yl, 10,11-dihydro-5H-dibenzo[a,d]cyclohepten-5-yl, 5H-dibenzo[a,d]cyclohepten-5-yl, 1,2,3,4-tetrahydro-1-naphthyl, 9H-xanthen-9-yl, 9H-thioxanthen-9-yl, 2-chloro-9H-thioxanthen-9-yl, 4H-chromanyl, diphenylmethyl, phenylcycloalkylmethyl wherein the bridgehead methylene may optionally be substituted with a hydroxy group and any of the phenyl or benzo-fused rings may be substituted with one or more $R_5$ groups wherein $R_5$ is selected from halogen, trifluoromethyl, lower alkyl, hydroxy or lower alkoxy groups; and $R_2$ and $R_3$, which may be the same or different, are hydrogen, lower alkyl, phenylalkyl ($C_1$–$C_5$), wherein the phenyl ring may be substituted with one or more $R_5$ groups or $NR_2R_3$ taken together are pyrrolidinyl, piperidinyl, morpholinyl, thiomorpholinyl, or 1-piperazinyl (where the 4-position may optionally be substituted with hydrogen, lower alkyl, hydroxy-substituted lower alkyl, amino-substituted lower alkyl, or acetoxy-substituted lower alkyl;

$R_4$ is hydrogen, hydroxyl or trimethylsilyloxy;

Ph is an unsubstituted phenyl group or a phenyl group substituted by one or more $R_5$ groups; and n is 2–4.

Pharmaceutical compositions effective as calcium channel blockers and therapeutic methods utilizing such compounds, particularly in the treatment of irritable bowel syndrome, are also disclosed.

4 Claims, No Drawings

2-AMINOMETHYLALKYNYLALKYL-1,3-DITHIANE DERIVATIVES

BACKGROUND OF THE INVENTION (a) Field of Invention

This invention relates to novel 2-aminomethylalkynylalkyl-1,3-dithiane derivatives, their pharmaceutically acceptable salts and their use in cardiovascular and gastrointestinal disorders in which calcium channel entry blockers are effective.

(b) State of the Art

Calcium ions apparently play a ubiquitous role in physiological body functions. They are involved in blood clotting and coagulation, cellular adhesion and integrity, membrane stability, enzyme activity, mediation of some of the effects of prostaglandins, neuronal transmission, glandular and cellular secretory functions, muscle contractions and many other physiological actions. Agents that act as calcium antagonists have a wide variety of therapeutic applications, e.g., as antihypertensives, coronary dilators, antiarrhythmics, smooth and skeletal muscle relaxants, antiinflammatory agents and local anesthetics, for example [R. G. Rahwan, M. F. Piasak, and D. T. Witiak, Canad. J. Physiol. Pharmacol., 57, 443 (1979); R. G. Rahwan and D. T. Witiak. in "Trace Metals in Health and Disease", N. Karasch, Ed., Raven Press, New York, p. 217]. These drugs are of particular value in the treatment of cardiac oxygen-deficiency diseases especially various forms of angina pectoris [H. Meyer, Annu. Rep. Med. Chem., 17, 71–77 (1982)]. Most of these agents are important cardiovascular drugs that inhibit smooth and cardiac muscle contraction. Comprehensive surveys of the pharmacology and potential therapeutic uses of calcium channel blockers have appeared [E. Wehinger and R. Gross, Annu. Rep. Med. Chem., 21, 85–94 (1986)].

The calcium channel blockers act mainly by inhibiting the influx of extracellular calcium into cells through the so-called "slow-calcium channel" in the cell membrane. Although inhibition of the slow inward calcium current is common to all calcium entry blockers, these agents often possess other major pharmacological actions that likely contribute to the overall effects [R. G. Rahwan, D. T. Witiak, and W. M. Muir, Annu. Rep. Med. Chem., 16 257–268 (1981)]. Thus $\beta_2$-adrenergic receptors with calcium channel blocking activity increase levels of smooth muscle cyclic-AMP, thus enhancing their smooth muscle relaxing properties (W. C. Bowman and M. J. Rand, "Textbook of Pharmacology", 2nd ed., Blackwell, Oxford. 1980. p. 22: 7). Among certain antiinflammatory drugs, calcium antagonistic actions correlate with their ability to inhibit prostaglandin synthesis associated with this property [B. J. Northover, Gen. Pharmacol., 8, 293 (1977)]. Indeed, the widely used antidiarrheal drug loperamide binds to calcium antagonist sites and it has been suggested that a substantial part of its therapeutic effectiveness is due to blockade of voltage-sensitive calcium channels in intestinal mucosal and smooth muscle cells [I. J. Reynolds, R. J. Gould and S. H. Snyder, J. Pharmacol. Exp. Ther., 231(3), 628–632 (1984)]. Thus, novel, selective, tissue specific calcium channel antagonists have potential utility as antidiarrheal and antispasmodic treatments for irritable bowel disease.

The majority of presently known calcium channel antagonists are structurally similar to four distinct classes of organic compounds, e.g., verapamil and its analogs, the dihydropyridines (e.g., nitrendepine), the benzothiazepines (e.g., diltiazem), and the diphenylalkylamines (e.g., cinnarazine). Apparently these disparate groups of compounds reduce smooth muscle contractility and secretory processes through either competitive interactions with a calcium channel site (receptor) or through sites allosterically linked to the channel [M. Spedding, M. Gittos, and A. K. Mir, J. Cardiovas. Pharmacol., 9, 461–468 (1987); A. K. Mir and M. Spedding, J. Cardiovas. Pharmacol., 9, 469–477 (1987)]. Completely new structures whose pharmacological action is primarily due to inhibition of calcium into contractile cells are relatively rare [H. Meyer, S. Kazda, and P. Bellemann, Annu. Rep. Med. Chem., 18, 79–88 (1983)].

The present invention provides a novel, structurally unique class of 2-aminomethylalkynylalkyl-1,3-dithiane derivatives which have calcium channel blocking activity.

SUMMARY OF THE INVENTION

The invention provides novel compounds of the Formulas I and II:

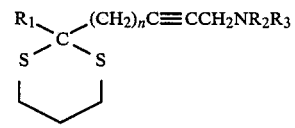

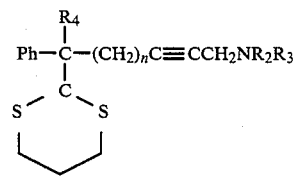

wherein:

$R_1$ is hydrogen, phenyl, 9H-fluoren-9-yl, 10,11-dihydro-5H-dibenzo [a,d]cyclohepten-5-yl, 9H-xanthen-9-yl, 9H-thioxanthen-9-yl, 2-chloro-9H-thioxanthen-9-yl, 5H-dibenzo[a,d]cyclohepten-5-yl, 1,2,3,4-tetrahydro-1-naphthyl, 4H-chromanyl, diphenylmethyl, phenylcycloalkylmethyl wherein the bridgehead methylene may optionally be substituted with a hydroxy group and any of the phenyl or benzo-fused rings may be substituted with one or more $R_5$ groups wherein $R_5$ is selected from halogen, trifluoromethyl, lower alkyl, hydroxy or lower alkoxy groups;

$R_2$ and $R_3$, which may be the same or different, are hydrogen, lower alkyl, phenylalkyl ($C_1$–$C_5$), wherein the phenyl ring may be substituted with one or more $R_5$ groups or $NR_2R_3$ taken together are pyrrolidinyl, piperidinyl, morpholinyl, thiomorpholinyl, or 1-piperazinyl (wherein the 4-position may optionally be substituted with hydrogen, lower alkyl, hydroxy-substituted lower alkyl, amino-substituted lower alkyl, or acetoxy-substituted lower alkyl);

$R_4$ is hydrogen, hydroxyl or trimethylsilyloxy;

Ph is an unsubstituted phenyl group and a phenyl group substituted by one or more $R_5$ groups; and n is 2 to 4.

As used herein, lower alkyl and alkoxy refer to groups having one to six carbons. The invention also includes the salts of the foregoing compounds, pharmaceutical compositions effective as calcium channel blockers and therapeutic methods utilizing such compounds, including treatment of irritable bowel syndrome.

DETAILED DESCRIPTION OF THE INVENTION

The invention is directed to 2-aminomthylalkynylalkyl-1,3-dithiane derivatives of Formulas I and II set forth above. The preferred compounds of the invention are those in which $R_1$ is 9H-xanthen-9-yl, 9H-thioxanthen-9-yl, 10,11-dihydro-5H-dibenzo[a,d]cyclohepten-5-yl, phenylcycloalkylmethyl and its derivative in which the bridgehead mthylene is substituted with a hydroxy group. The most preferred $R_2$ and $R_3$ groups are ethyl. Hydroxy is the most preferred $R_4$ group. In preferred practice n is 2 or 3.

Among the preferred compounds are 2-(5-diethylaminopent-3-ynyl)-2-(9-hydroxy-9H-xanthen-9-yl)-1,3-dithiane, 2-(5-diethylaminopent-3-ynyl)-2-diphenylmethylhydroxy-1,3-dithiane, 2-(5-piperidinylpent-3-ynyl)-2-(9-hydroxy-9H-xanthen-9-yl)-1,3-dithiane, 2-[5-(4-methylpiperazinyl)pent-3-ynyl]-2-(9-hydroxy-9H-xanthen-9-yl)-1,3-dithiane, 2-(6-diethylaminohex-4-ynyl)-2-(9-hydroxy-9H-xanthen-9-yl)-1,3-dithiane, 2-(5-dimethylaminopent-3-ynyl)-2-(9-hydroxy-9H-thioxanthen-9-yl)-1,3-dithiane, 2-(5-diethylaminopent-3-ynyl)-2-(9-hydroxy-9H-thioxanthen-9-yl)-1,3-dithiane, 2-(5-diethylaminopent-3-ynyl)-2-(9-hydroxy-9H-fluoren-9-yl)-1,3-dithiane, 2-(5-diethylaminopent-3-ynyl)-2-(2-chloro-9-hydroxy-9H-thioxanthen-9-yl)-1,3-dithiane, 2-(6-dipropylaminohex-4-ynyl)-2-(9-hydroxy-9H-xanthen-9-yl)-1,3-dithiane, 2-(6-dipropylaminohex-4-ynyl)-2-(9-hydroxy-9H-thioxanthen-9-yl)-1,3-dithiane, 2-(5-diethylaminopent-3-ynyl)-2-(5-hydroxy-5H-dibenzo[a,d]cyclohepten-5-yl)-1,3-dithiane, 2-(7-dipropylaminohept-5-ynyl)-2-(9-hydroxy-9H-xanthen-9-yl)-1,3-dithiane, 2-(5-diethylaminopent-3-ynyl)-2-(5-hydroxy-10,11-dihydro-5H-dibenzo[a,d]cyclohepten-5-yl)-1,3-dithiane, and 2-[5-[2-(3,4-dimethoxyphenyl)ethyl]methylamino-1-phenyl-1-trimethylsilyloxyhex-4-ynyl]-1,3-dithiane.

The compounds of the invention act as calcium antagonists and have a wide variety of therapeutic applications, particularly as cardiovascular (antihypertensive) and gastrointestinal agents. As a result of their action on colonic motility, and their antispasmodic, and antisecretory effects in the gastrointestinal tract, coupled with their antidiarrheal actions, they are of particular benefit in the treatment of irritable bowel syndrome.

To the extent the compounds of the invention may exist as optical isomers, both isomers and the racemic mixture are to be understood to be included in the invention. In addition, all possible other isomeric forms of the compounds of the invention are within the ambit of this invention.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The compounds of this invention may be administered orally or parenterally in conventional dosage unit forms such as tablets, capsules, injectables, aerosols, or the like, by incorporating the appropriate dose of a compound of formula I or II with carriers according to accepted pharmaceutical practices.

Preferably a compound or an acid addition salt thereof is administered orally to an animal organism in a tablet or capsule comprising an amount sufficient to produce the desired activity of a calcium channel blocker. Each dosage unit will contain the active ingredient in an amount of about 10 mg. to about 150 mg., preferably from about 40 mg. to about 100 mg. Advantageously equal doses will be administered 3 to 4 times daily with the daily dosage regimen being about 120 mg. to about 800 mg., preferably from about 160 mg. to about 400 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or nonaqueous liquid suspension.

The compounds (Formula I) of the invention can be prepared by Mannich condensation of a 2-ethynylalkyl-1,3-dithiane with formaldehyde and the appropriate amine, lithiation and addition to the requisite ketonic reagent. Alternatively, the Mannich product of amine, formaldehyde and ethynylalkanol is oxidized to the aldehyde which is subsequently condensed with 1,3-propanedithiol, the resulting 1,3-dithiane is lithiated, and then added to the ketone. Another route entails a similar sequence in which the ethynylalkanol is sequentially oxidized to the aldehyde, converted to the dithiane, subjected to Mannich condensation and then transformed to a lithio derivative which is added to the ketone. In other variations, an ethynylalkyl halide (protected or unprotected) is added to a 2-aryl-2-lithio-1,3-dithiane or 2-lithio-1,3-dithiane and the resulting unprotected ethynyl derivative is subjected to Mannich condensation which in the case of the monosubstituted dithiane may be litiated and added to an appropriate ketone. Alternatively, an ethynylalkylaldehyde is added to a Grignard reagent to give a secondary alcohol which is oxidized to a ketone that is reacted with 2-lithio-1,3-dithiane. The resulting product, after protection, is subjected to Mannich aminomethylation to afford a compound of Formula II.

The following examples are illustrative of the invention.

EXAMPLES

Example I

Pent-4-ynal. To a solution of oxalyl chloride (9.12 mL, 104.6 mmol) dissolved in methylene chloride (200 mL) at −78° C. was added dimethylsulfoxide (14.8 mL, 209.2 mmol) dissolved in methylene chloride (40 mL) over 20 minutes. The reaction solution was kept under a positive pressure of argon until workup. The reaction mixture was stirred for an additional 30 minutes when pent-4-yn-1-ol (8.00 g, 95.1 mmol) dissolved in methylene chloride (80 mL) was added over 10 minutes. Stirring was continued for an additional 60 minutes. Triethylamine (66.2 mL, 475.5 mmol) was added at −78° C. and the reaction mixture was stirred for 60 minutes and then allowed to warm to 10° C. over an additional hour. Water (200 mL) was added and the two layers were separated. The aqueous layer was acidified with 1% aqueous hydrochloric acid (saturated with NaCl) and then back-extracted with additional methylene chloride (3×100 mL). The combined organic layers were washed with 1% hydrochloric acid (in saturated brine solution, 6×100 mL) and 5% sodium bicarbonate solution (2×50 mL). The aqueous extracts were back-extracted with methylene chloride (2×100 mL) and the combined organic extracts were washed with brine (2×50 mL) and dried ($MgSO_4$). The solvent was removed by rotary evaporation (30° C. water bath) to give 7.18 g (92%) of pent-4-ynal as a yellow oil. $^1H$ NMR ($CDCl_3$): δ9.8 (s, 1H), 2.8–2.3 (m, 4H), 2.0–1.9 (t, 1H); IR (neat): 3296 (s), 2926, 2848, 1725(s) $cm^{-1}$; TLC (silica gel, 90% hexane: 10% ethyl acetate) Rf=0.43.

2-(But-3-ynyl)-1,3-dithiane.

To a solution of pent-4-ynal (6.99 g, 85.1 mmol) dissolved in methylene chloride (85 mL) was added 1,3-propanedithiol (8.54 mL, 85.1 mmol). The solution was stirred at room temperature for 1 hour and then cooled to −20° C. Boron trifluoride etherate (10.46 mL, 85.1 mmol) was added and, after warming to room temperature, the solution was stirred for 16 hours. The solution was washed with water (2×20 mL) and the aqueous extract was washed with additional methylene chloride (2×40 mL). The combined organic extracts were washed with 10% potassium hydroxide solution (4×30 mL) and the aqueous extract was washed with additional methylene chloride (2×40 mL). The combined organic extracts were washed with 10% potassium hydroxide solution (4×30 mL) and the aqueous extract was back-extracted with methylene chloride (2×40 mL). The combined organic extracts were washed with brine (2×40 mL) and dried ($K_2CO_3$). The solvent was removed by rotary evaporation to afford 9.14 g (62%) of 2-(but-3-ynyl)-1,3-dithiane as a pale yellow oil. $^1H$ NMR ($CDCl_3$)δ: 4.2 (t, 1H), 3.1–2.8 (m, 4H), 2.6–2.4 (m, 1H), 2.3–2.0 (m, 6H); IR (neat): 3286, 2908, 1421, 1272, 907 $cm^{-1}$; GC retention time=3.11 min (88% area); TLC (silica gel, 90% hexane: 10% ethyl acetate) Rf=0.74.

2-[5-(4-Methylpiperazinyl)pent-3-ynyl]-1,3-dithiane Dioxalate.

A mixture of paraformaldehyde (0.24 g, 8.24 mmol), cupric acetate (0.10 g), and 1-methylpiperazine (0.908 g, 9.06 mmol) dissolved in dioxane (5 mL) was heated in an oil bath at 55° C. for 1 hour. 2-(But-3-ynyl)-1,3-dithiane (1.42 g, 8.24 mmol) dissolved in dioxane (2 mL) was added to the green solution and heating at 95° C. was continued for 3 hours. After cooling to room temperature the reaction mixture was poured into 10% potassium hydroxide solution (5 mL) and the thin brown precipitate which formed was filtered and washed with diethyl ether (75 mL). The organic layer was washed with brine (3×20 mL) and dried ($K_2CO_3$). The solution was evaporated to dryness to give 2.18 g of an orange oil which was chromatographed on silica gel eluting with a gradient consisting of 95:5:3/hexane:ethyl acetate:triethylamine to 50:50:3/hexane:ethyl acetate:triethylamine to give 2.16 g of an orange-brown oil. The oil was further purified by Kugelrohr distillation (b.p. 205° C., 5 mm Hg) to give 1.72 g (73%) of 2-[5-(4-methylpiperazinyl)pent-3-ynyl]-1,3-dithiane as a pale yellow oil: $^1H$ NMR ($CDCl_3$)δ: 4.13 (t, 1H), 3.26 (s, 2H) 2.88–2.83 (m, 4H), 2.60–2.39 (m, 8H), 2.30 (s, 3H), 2.14–1.89 (m, 6H); IR (neat) 2917, 2803, 1456, 1282, 1165, 1143, 1010, 907 $cm^{-1}$; GC retention time=10.04 min (100% area); TLC (silica gel, 8% triethylamine:30% ethyl acetate:62% hexane) Rf=0.46.

To a solution of the dithiane (0.64 g, 2.249 mmol) in tetrahydrofuran (8 mL) was added a solution of oxalic acid (0.4050 g, 4.498 mmol) in tetrahydrofuran (5 mL). The white solid which immediately precipitated from the solution was recrystallized from tetrahydrofuran:methylene chloride (4:1). The solid was collected, washed with tetrahydrofuran and dried in vacuo in a drying pistol at 60° C. overnight to give 0.98 g (93%) of the dioxalate salt: m.p. 212°–214° C. $^1H$ NMR ($Me_2SO$-$d_6$)δ: 8.10 (br s, 4H), 4.13 (t, 1H), 3.33 (s, 2H), 3.17 (s, 4H), 2.85–2.76 (m, 4H), 2.73 (s, 3H), 2.71–2.68 (m, 4H), 2.39–2.35 (m, 2H), 2.04–1.98 (m, 1H), 1.91–1.83 (m, 2H), 1.75–1.68 (m, 1H); $^{13}C$ NMR ($Me_2SO$-$d_6$)δ: 162.46, 84.38, 74.16, 52.53, 48.10, 45.64, 44.69, 42.28, 34.29, 28.47, 25.37, 22.12, 15.66; TLC (silica gel, 8% triethylamine:30% ethyl acetate:62% hexane) Rf=0.16; Calcd for $C_{18}H_{28}N_2O_8S_2$: C: 46.53; H: 6.08; N: 6.02. Found: C: 46.48; H: 6.12; N: 5.98.

2-[5-(4-Methylpiperazinyl)pent-3-ynyl]-2-(9-hydroxy-9H-xanthen-9-yl)-1,3-dithiane Dioxalate.

To a solution of 2-[5-(4-methylpiperazinyl)pent-3-ynyl]-1,3-dithiane (1.31 g, 2.72 mmol) in tetrahydrofuran (6 mL) under argon atmosphere was added dropwise at −40° C. 2.5M n-butyllithium (1.30 mL, 3.26 mmol). The solution was stirred at −25° to −20° C. under argon atmosphere for 2.5 hours. The yellow reaction solution was cooled to −78° C. and xanthone (0.53 g, 2.72 mmol) dissolved in tetrahydrofuran (7 mL) was added. The solution immediately became deep blue and within 2 minutes after addition became orange. The solution was stirred at −70° C. to −55° C. for 1 hour and then stored at −15° C. for 18 hours. The reaction solution was then poured into water (30 mL) and the two layers were separated. The aqueous layer was extracted with methylene chloride (3×40 mL) and the combined organic extracts were washed with 10% potassium hydroxide solution (2×30 mL), brine (1×30 mL) and dried ($K_2CO_3$). The solvent was removed to afford 2.47 g of a yellow-orange oil. The oil was chromatographed on short path TLC silica gel (42 g) eluting with 8% triethylamine:30% ethyl acetate:62% hexane to give 0.76 g (58%) of 2-[5-(4-methylpiperazinyl)pent-3-ynyl]-2-(9-hydroxy-9H-xanthen-9-yl)-1,3-dithiane as a pale yellow foam. $^1H$ NMR ($CDCl_3$)δ: 7.93–7.12 (m, 8H), 2.97–2.81 ( , 4H), 4.60 (s, 1H), 2.55–2.33 (m, 12H), 2.06 (s, 3H), 1.90–1.5 (m, 4H); TLC (silica gel, 8% triethylamine:30% ethyl acetate:62% hexane) Rf=0.25.

To a solution of the dithiane (0.65 g, 1.35 mmol) in tetrahydrofuran (15 mL) was added a solution of oxalic acid (0.2435 g, 2.70 mmol) in tetrahydrofuran (5 mL). An off-white solid immediately precipitated from the solution. The solid was recrystallized from ethyl acetate:methanol (2:3), washed with diethyl ether and dried in vacuo in a drying pistol at 60° C. overnight to give 0.532 g (59%) of the dioxalate salt: m.p. 201°–202° C. $^1$H NMR (Me$_2$SO-d$_6$+D$_2$O)δ: 7.92–7.16 (m, 8H), 3.25–3.12 (m, 6H), 2.76 (s, 3H), 2.66–2.40 (m, 8H), 1.91–1.40 (m, 6H); IR (KBr): 3427, 2923, 2499, 1720, 1625, 1450, 1205, 961, 912, 775 cm$^{-1}$; TLC (silica gel 8% triethylamine:30% ethyl acetate:62% hexane) Rf=0.16; Calcd for C$_{31}$H$_{36}$N$_2$O$_{10}$S$_2$: C: 56.34; H: 5.50; N: 4.23. Found: C: 56.08; H: 5.59; N: 4.19.

The following compounds, the melting points of which are in parenthesis, were also prepared by this general sequence:

2-[5-(4-Methylpiperazinyl)pent-3-ynyl]-1,3-dithane Dioxalate (212°–214° C.),

2-[5-[4-(2-Hydroxyethyl)piperazinyl]pent-3-ynyl]-1,3-dithiane Dioxalate (195°–196° C.), 2-[5-[2-(3,4-Dimethoxyphenyl)ethyl]methylaminopent-3-ynyl]-1,3-dithiane Oxalate (127°–128.5° C.), 2-[5-(4-Phenylbutyl)methylaminopent-3-ynyl]-1,3-dithiane Oxalate (114°–114.5° C.), 2-[5-(4-Phenylbutyl)methylaminopent-3-ynyl]-2-(9-hydroxy-9H-xanthen-9-yl)-1,3-dithiane (126°–127° C.), 2-[5-(4-Phenylbutyl)methylaminopent-3-ynyl]-2-(9-hydroxy-9H-thioxanthen-9-yl)-1,3-dithiane (108°–109° C.), and 2-(5-Diethylaminopent-3-ynyl)-2-(5-hydroxy-5H-dibenzo[a,d]cyclohepten-5-yl)-1,3-dithiane Oxalate (124°–125° C.).

EXAMPLE II

6-Diethylaminohex-4-yn-1-ol.

A mixture of paraformaldehyde (21.42 g, 714 mmol), diethylamine (82.2 mL, 801 mmol) and copper(11) acetate (2 g) was heated at 60° C. in dioxane (120 mL). After 1.4 hours pent-4-yn-1-ol (60 g, 714 mmol) was added and the mixture was heated at 95° C. for 3 hours. The cooled reaction mixture was poured onto 10% potassium hydroxide (120 mL) and the resulting mixture was filtered through Celite which was washed with diethyl ether. The organic layer was separated and washed with water (3×120 mL). The aqueous extract was back-extracted with methylene chloride (3×100 mL). The combined organic layers were washed with brine, dried (MgSO$_4$), and evaporated at reduced pressure. The residue was Kugelrohr distilled to afford 102 g (99%) of the product as an oil. $^1$H NMR (CDCl$_3$)δ: 1.13 (t, 6H), 1.72 (quintet, 2H), 2.31 (t, 2H), 2.55 (q, 4H), 3.38 (d, 2H), 3.68 (t, 2H), 3.95 (s, 1H) ppm.

6-Diethylaminohex-4-ynal.

To a solution of oxalyl chloride (32 mL, 352 mmol) in methylene chloride (800 mL) under argon atmosphere at −78° C. was added dimethylsulfoxide (54.4 mL, 704 mmol) in methylene chloride (40 mL) over 15 minutes. After stirring for 5 minutes 6-diethylaminohex-4-yn-1-ol (50 g, 296 mmol) dissolved in methylene chloride (60 mL) was added dropwise over 35 minutes. After stirring 20 minutes triethylamine (224 mL, 1600 mmol) was added at −78° C. over 30 minutes and the reaction mixture was allowed to warm to room temperature. Water (400 mL) was added, the layers were separated, and the organic layer was washed with water (2×200 mL). The aqueous layer was back-extracted with methylene chloride (2×150 mL) and the combined organic extracts were washed with brine and dried (MgSO$_4$). Removal of solvent under reduced pressure gave a quantitative yield of the product as an oil. $^1$H NMR (CDCl$_3$) δ: 1.13 (t, 6H), 2.48–2.58 (m, 6H), 2.65 (q, 2H), 3.39 (d, 2H), 9.80 (s, 1H) ppm.

2-(5-Diethylaminopent-3-ynyl)-1,3-dithiane.

To a solution of 6-diethylaminohex-4-ynal (50 g, 290 mmol) in methylene chloride (600 mL) was added 1,3-propanedithiol (30 mL, 290 mmol). The solution was stirred at room temperature for 1 hour and then cooled in an ice-bath. Boron trifluoride etherate (40 mL, 290 mmol) was added and the solution was stirred at room temperature overnight. The mixture was washed with water (150 mL), 10% potassium hydroxide solution (2×300 mL), brine (3×100 mL) and dried (MgSO$_4$). Evaporation of the solvent afforded an oil which was Kugelrohr distilled (oven 120° C., 0.1 mm Hg) to give 20 g of product. The residue was chromatographed on basic alumina (activity I) eluting with methylene chloride and the oil was redistilled by Kugelrohr to afford 14 g (45%) of product. $^1$H NMR (CDCl$_3$) δ: 1.14 (t, 6H), 1.80–1.90 (m, 1H), 1.91 (q, 2H), 2.05–2.15 (m, 1H), 2.43 (t, 2H), 2.52 (q, 4H), 2.81–2.90 (m, 4H), 3.39 (d, 2H), 4.17 (t, 1H) ppm.

2-(5-Diethylaminopent-3-ynyl)-2-(9-hydroxy-9H-xanthen-9-yl)-1,3-dithiane.

2-(5-Diethylaminopent-3-ynyl)-1,3-dithiane (5.0 g, 19.4 mmol) was stirred with 100 mL THF at −78° C. under nitrogen and 2.5M n-BuLi (10 mL, 25 mmol) in hexane was added. After stirring 1 hour the temperature was brought to −20° C. and TMEDA (3.75 mL, 25 mmol) was added. After 0.5 hour the temperature was brought to −78° C. and 4.18 g (21.3 mmol) of xanthone was added as a solid. The mixture was stirred 3 hours before pouring onto 100 mL water. The organics were separated, the aqueous portion extracted with methylene chloride (2×50 mL), the combined organics dried (MgSO$_4$) and evaporated at reduced pressure. The residue was chromatographed on 150 g silica gel (9:1, pet ether: EtAc followed by 9:1:0.01; 9:1:0.02; 9:1:0.04; 8:2:0.04; 6:4:0.04 pet ether: EtAc: triethylamine) to give about 7 g of purified product as an oil, which was crystallized from benzene/pet ether to give 4.5 g (51%), mp 127°–128° C. Analytical TLC (silica 92:5:3, pet ether: EtAc: triethylamine) Rf.08; $^1$H NMR (CDCl$_3$) δ 1.02 (t, J=7.2 Hz, 6H), 1.6–1.8 (m, 3H), 1.9–2.0 (m, 1H), 2.37–2.6 (m, 8H), 3.28 (t, J=2.2 Hz, 2H), 3.41 (s, 1H), 7.14–7.4 (m, 6H), 7.9–7.95 (m, 2H); IR(KBr) 1600, 1477, 1447, 1285, 1239, 764.

Analysis calcd. for C$_{26}$H$_{31}$NO$_2$S$_2$: C, 68.82; H, 6.89; N, 3.10; S, 14.13. Found: C, 68.90; H, 6.93; N, 3.03; S, 14.06.

The following compounds (mp in parentheses) were also prepared by this general route:

2-(5-Diethylaminopent-3-ynyl)-2-(9-hydroxy-9H-xanthen-9-yl)-1,3-dithiane (127.5°–129° C.), 2-(5-Diethylaminopent-3-ynyl)-2-(α-cyclohexyl-α-hydroxybenzyl)-1,3-dithiane Hemioxalate (172°–173° C.), 2-(5-Diethylaminopent-3-ynyl)-2-(α-cyclopentyl-α-hydroxybenzyl-1,3-dithiane Oxalate (139°–140° C.), 2-(5-Diethylaminopent-3-ynyl)-1,3-dithiane · Oxalate (93°–94° C.), 2-(5-Diethylaminopent-3-ynyl)-2-(α-hydroxy-α-phenylbenzyl)-1,3-dithiane Oxalate (118°–120° C.), 2-(5-Diethylaminopent-3-ynyl)-2-(1-hydroxy-1,2,3,4-tetrahydro-1-naphthyl)-1,3-dithiane Hemioxalate (155°–158° C.), 2-[5-(2-Phenylethyl)methylaminopent-3-ynyl]-2-(α-cyclohexyl-α-hydroxybenzyl)-1,3-dithiane Oxalate (85°–87° C.), 2-(5-Diethylaminopent-3-ynyl)-2-(α-hydroxy-α-methylbenzyl)-1,3-dithiane (76°–78° C.), 2-[5-(2-Phenylethyl)methylaminopent-3-ynyl]-2-(α-hydroxy-α-phenylbenzyl)-1,3-dithiane Oxalate Hemihydrate (78°–81° C.), 2-[5-(2-Phenylethyl)methylaminopent-3-ynyl]-1,3-dithiane Oxalate (76°–77° C.), 2-(5-Diethylaminopent-3-ynyl)-2-benzyl-1,3-dithiane Oxalate (115°–117° C.), 2-(5-Diethylaminopent-3-ynyl)-2-benzhydryl-1,3-dithiane Oxalate Hydrate (151°–152° C.), 2-(5-Piperidinylpent-3-ynyl)-2-(9-hydroxy-9H-xanthen-9-yl)-1,3-dithiane (1,3-dithiane (170° C.), 2-(5-Ethylmethylaminopent-3-ynyl)-1,3-dithiane Oxalate (94°–96° C.), 2-(5-Piperidinylpent-3-ynyl)-1,3-dithiane Oxalate (151°–152° C.), 2-(5-Dimethylaminopent-3-ynyl)-1,3-dithiane Oxalate (136°–137° C.), 2-(5-Pyrrolidinylpent-3-ynyl)-1,3-dithiane Oxalate (102°–102.5° C.), 2-(5-Dimethylaminopent-3-ynyl)-2-(9-hydroxy-9H-xanthen-9-yl)-1,3-dithiane (186°–187° C.), 2-[5-(3Phenylpropyl)methylaminopent-3-ynyl]-2-(2-chloro-9-hydroxy-9H-thioxanthen-9-yl)-1,3-dithiane Hemioxalate (151°–152.5° C.), 2-(5-Dimethylaminopent-3-ynyl)-2-(2-chloro-9-hydroxy-9H-thioxanthen-9-yl)-1,3-dithiane (163°–164.5° C.), 2-(5-Dimethylaminopent-3-ynyl)-2-(9-hydroxy-9H-thioxanthen-9-yl)-1,3-dithiane (183.5°–184.5° C.), 2-(5-Dimethylaminopent-3-ynyl)-2-(9-hydroxy-9H-fluoren-9-yl)-1,3-dithiane (175°–181° C.), 2-(5-Ethylmethylaminopent-3-ynyl)-2-(9-hydroxy-9H-xanthen-9-yl)-1,3-dithiane (152°–153° C.), 2-(5-Ethylmethylaminopent-3-ynyl)-2-(9-hydroxy-9H-thioxanthen-9-yl)-1,3-dithiane (163°–164° C.), 2-(5-Ethylmethylaminopent-3-ynyl)-2-(2-chloro-9-hydroxy-9H-thioxanthen-9-yl)-1,3-dithiane (159°–160.5° C.), 2-[5-(Benzylmethylaminopent-3-ynyl]-2-(α-hydroxy-α-phenylbenzyl)-1,3-dithiane Oxalate Hemihydrate (165°–170° C. dec), 2-[5-(Benzylmethylaminopent-3-ynyl]-1,3-dithiane Oxalate (114.5°–116° C.), 2-[5-(3-Phenylpropyl)methylaminopent-3-ynyl]-1,3-dithiane Oxalate (120°–125° C.), 2-[5-(1-Naphthylmethyl)methylaminopent-3-ynyl]-1,3-dithiane Oxalate (126°–129° C.), 2-[5-(2-Naphthylmethyl)methylaminopent-3-ynyl]-1,3-dithiane Oxalate (118°–125° C.), 2-[5-(1-Naphthylethyl)methylaminopent-3-ynyl]-1,3-dithiane Oxalate (155°–156° C.), 2-[5-(2-Naphthylethyl)]methylaminopent-3-ynyl]-1,3-dithiane Oxalate (135°–136° C.), 2-[5-(3-Phenylpropyl)methylaminopent-3-ynyl]-2-(9-hydroxy-9-phenylbenzyl)-1,3-dithiane Oxalate (70°–73° C.), 2-[5-(3-Phenylpropyl)methylaminopent-3-ynyl]-2-(9-hydroxy-9H-xanthen-9-yl)-1,3-dithiane (148°–149° C.), 2-[5-(3-Phenylpropyl)methylaminopent-3-ynyl]-2-(9-hydroxy-9H-thioxanthen-9-yl)-1,3-dithiane (130°–131° C.), 2-(5-Diethylaminopent-3-ynyl)-2-(9-hydroxy-9H-thioxanthen-9-yl)-1,3-dithiane Oxalate (166°–169° C.), 2-(5-Ethylmethylaminopent-3-ynyl)-2-(9-hydroxy-9H-fluoren-9-yl)-1,3-dithiane (150.5°–151.5° C.), 2(5-Diethylaminopent-3-ynyl)-2-(9-hydroxy-9H-fluoren-9-yl)-1,3-dithiane (158°–159° C.), 2-(5-Diethylaminopent-3-ynyl)-2-(2-chloro-9-hydroxy-9H-thioxanthen-9-yl)-1,3-dithiane Oxalate (177°–178° C.), 2-(5-Piperidinylpent-3-ynyl)-2-(9-hydroxy-9H-thioxanthen-9-yl)-1,3-dithiane (167°–168° C.), 2-(5-Piperidinylpent-3-ynyl)-2-(2-chloro-9-hydroxy-9H-thioxanthen-9-yl)-1,3-dithiane (175°–176° C.), 2-(5-Piperidinylpent-3-ynyl)-2-(9-hydroxy-9H-fluoren-9-yl)-1,3-dithiane (149°–153° C.), 2(5-Diethylaminopent-3-ynyl)-2-(4-hydroxy-4H-chromanyl)-1,3-dithiane (92°–93° C.), and 2-(5-Diethylaminopent-3-ynyl)-2-(5-hydroxy-10,11-dihydro-5H-dibenzo[a,d]cyclohepten-5-yl)-1,3-dithiane Oxalate (78°–81° C.).

EXAMPLE III

Hex-5-ynal.

To a solution of oxalyl chloride (20.4 mL, 0.22 mmol) dissolved in methylene chloride (500 mL) under argon atomosphere at −78° C. was added dropwise dimethylsulfoxide (34.7 mL, 0.44M). After stirring 15 minutes hex5-yn-1-ol (20 g, 0.204M) dissolved in methylene chloride was added dropwise. After stirring 1.5 hours at −78° C. triethylaminne (140 mL, 1M) was added and the reaction mixture was allowed to warm to 10° C. Water (200 mL) was added, the layers were separated, and the organic layer was washed with 1% hydrochloric acid solution (3×200 mL), brine and dried (K$_2$CO$_3$). Evaporation of the solvent under reduced pressure afforded the product in quantitative yield.

2-(Pent-4-ynyl)-1,3-dithiane.

Hex-5-ynal (20 g, 0.2M) and 1,3-propanedithiol (20 mL, 0.2 mmol) were stirred in 300 mL methylene chloride at 0°–5° C. and HCl(g) was bubbled into the solution for 10 minutes when it became cloudy. The mixture was stirred 2 days after which it was poured onto 100 mL of 10% KOH. The organics were washed again with 10% KOH (25 mL), then brine, and dried (MgSO$_4$) before evaporation at reduced pressure. The residue was Kugelrohr distilled at 0.1 mm, oven 110° C. to give 27 g of product (72%). $^1$H NMR (CDCl$_3$) δ 1.7–1.8 (m, 2H), 1.8–1.95 (m, 3H), 1.99 (t, J=2.6 Hz, 1H), 2.2–2.25 (m, 2H), 2.8–2.95 (m, 4H), 4.06 (t, J=6.9 Hz, 1H).

2-(6-Diethylaminohex-4-ynyl)-1,3-dithiane Oxalate.

Diethylamine (1.55 mL, 15 mmol), paraformaldehyde (0.45 g, 15 mmol), and 63 mg copper(II) acetate were heated at 60° C. in 6 mL dioxane. After 1 hour 2.79 g (15 mmol) of 2-(pent-4-ynyl)-1,3-dithiane was added and the temperature adjusted to 85°–90° C. where it was kept overnight. The cooled reaction mixture was poured onto 10% KOH (10 mL) and filtered through Celite, which was subsequently washed with 50 mL of ether. The organics were separated and washed with water (3×20 mL), the aqueous portions were back extracted with methylene chloride (3×20 mL), and the combined organics washed with brine, dried (MgSO$_4$), and evaporated at reduced pressure. The residue was Kugelrohr distilled at 1 mm, oven 140°–145° C., to give 3.08 g (76%) of 2-(6-diethylaminohex-4-ynyl)-1,3-dithiane. Analytical TLC (silica, 92:5:3, pet ether: EtAc: Et$_3$N) Rf.26; IR (neat) 1635(w), 1455, 1424, 1375, 1329, 1272, 1198, 1909, 982, 910, 768 cm−1; $^1$H NMR (CDCl$_3$) δ 0.99 (t, J=7.2 Hz, 6H), 1.6–1.7 (m, 2H), 1.75–1.9 (m, 3H), 2.0–2 (m, 1H), 2.1–2.2 (m, 2H), 2.46 (q, J=7.2 Hz, 4H), 2.7–2.9 (m, 4H), 330 (t, J=2.1 Hz, 2H), 3.99 (t, J=6.8 Hz, 1H). A portion of the product was converted into its oxalate salt and recrystallized from THF to give the analytical sample, mp 140°–145° C.

Analysis calcd. for C$_{14}$H$_{25}$NS$_2$C$_{H2}$O$_6$: C, 53.15; H, 7.53; N, 3.89; S, 17.73. Found: C, 53.26; H, 7.59; N, 3.83; S, 17.69.

2-(6-Diethylaminohex-4-ynyl)-2-(9-hydroxy-9H-xanthen-9-yl)-1,3-dithiane.

2.5M n-BuLi in hexane (1.8 mL, 4.4 mmol) was added to 1.0 g (3.7 mmol) of 2-(6-diethylaminohex-4-ynyl)-1,3-dithiane, in 25 mL of THF at −40° C. under argon and stirred 10 minutes before adjusting the temperature to −20° C. After 2 hours 0.86 g (4.4 mmol) of xanthone was added as a solid and the mixture was kept at −20° C. overnight. The reaction was poured onto 30 mL of water and the organics separated. The aqueous portion was extracted with methylene chloride (3×20 mL) and the combined organics washed with brine, dried (MgSO$_4$), and evaporated at reduced pressure to an oil that partially solidified. The residue was chromatographed on 75 g silica gel (9:1, pet ether: EtAc, 9: 1:01, then 9: 1:0.2, 9:1:0.4, and 8:2:0.4) pet ether:EtAc:Et$_3$N to give 320 mg (19%) product that was recrystallized from EtAc to give the analytical sample, mp 193°–193.5° C. Analytical tlc (silica, 92:5:3, pet ether-:EtAc:Et$_3$N) Rf.22; IR (KBr) 3500(b), 1599(w), 1468, 1439, 1280, 1234, 1090(w), 1074(w), 758 cm$^{-1}$; $^1$H NMR (d$_6$-DMSO) δ 0.858 (t, J=7.2 Hz, 6H), 1.15–1.25 (m, 2H), 1.5–1.65 (m, 3H), 2.25 (q, J=7.2 Hz, 4H), 2.5–2.6 (m, 2H), 3.15 (s, 2H), 3.2–3.2 (m, 3H), 7.05–7.2 (m, 4H), 7.27–7.35 (m, 2H), 7.89 (d, J=6.4 Hz, 2H).

Analysis calcd. for C$_{27}$H$_{33}$NO$_2$S$_2$:C, 69.33; H, 7.11; N, 3.01; S, 1371. Found: C, 69.21; H, 7.16; N, 2.95; S, 13.65.

The following compounds (mp in parentheses) were prepared by this general procedure:
2-(6-Benzylmethylaminohex-4-ynyl)-1,3-dithiane Oxalate (89°–92° C.),
2-8 6-(2-Phenylethyl)methylaminohex-4-ynyl]-1,3-dithiane Oxalate (110°–111° C.),
2-(6-Diethylaminohex-4-ynyl)-1,3-dithiane Oxalate (140°–145° C.),
2-(6-Diethylaminohex-4-ynyl)-2-(9-hydroxy-9H-fluoren-9-yl)-1,3-dithiane (153°–154.5° C.),
2-(6-Dipropylaminohex-Jb 4-ynyl)-2-(9-hydroxy-9H-xanthen-9-yl)-1,3-dithiane (147°–147.5° C.),
2-(6-Dipropylaminohex-4-ynyl)-2-(9-hydroxy-9H-fluoren-9-yl)-1,3-dithiane (147°–148° C.),
2-(6-Dipropylaminohex-4-ynyl)-2-(9-hydroxy-9H-thioxanthen-9-yl)-1,3-dithiane (150°–151° C.),
2-(6-Ethylisopropylaminohex-4-ynyl)-2-(9-hydroxy-9H-xanthen-9-yl)-1,3-dithiane (141°–142.5° C.), and
2-(6-Disopropylaminohex-4-ynyl)-2-(9-hydroxy-9H-xanthen-9-yl)-1,3-dithiane (113°–114.5° C.).

EXAMPLE IV

2-Phenyl-1,3-dithiane.

Benzaldehyde (11.5 mL, 112 mmol and 1,3-propanedithiol (120 mL, 92.5 mmol) were stirred in methylene chloride (200 mL) at 0° C. and HCl(g) was bubbled into the solution followed by addition of zinc chloride (9 g). The mixture was stirred overnight after which it was poured onto 10% potassium hydroxide solution. The layers were separated and the organic extract was washed with 10% potassium hydroxide solution, water, brine and dried (MgSO$_4$). Evaporation of solvent at reduced pressure afforded an oil which crystallized upon standing and was recrystallized from diethyl ehter to give 16.2 g (89%) of product. $^1$H NMR (CDCl$_3$) δ: (m, 2H), 5.16 (s, 1H), 7.25–7.36 (m, 3H), 7.45–7.48 (m, 2H) ppm.

4-Bromobut-1-yne.

To a solution of but-3-yn-1-ol (10 g, 0.14M) in diethyl ether (75 mL) cooled in an ice-bath was added phosphorus tribromide (6.7 mL, 0.071M) in diethyl ether (25 mL) over 30 minutes. The mixture was heated at reflux for 2 hours, cooled and poured onto ice. The aqueous portion was extracted with diethyl ether (50 mL) and the combined organic extracts were washed with saturated sodium bicarbonate solution, water, brine and dried (MgSO$_4$). Removal of solvent under reduced pressure gave 11 g (59%) of the product. $^1$H NMR (CDCl$_3$) δ: 2.12 (t, J=2.62 Hz, 1H), 2.76 (t, J=7.20 Hz, J=2.60 Hz, 1H), 2.77 (t, J=7.16 Hz, J=2.61 Hz, 1H), 3.45 (t, J=7.18 Hz, 2H) ppm.

2-(But-3-ynyl)-2-phenyl-1,3-dithiane.

To a solution of 2-phenyl-1,3-dithiane (6.4 g, 32.7 mmol) in tetrahydrofuran (100 mL) at −40° C. under argon atmosphere was added 2.5M n-butyllithium (13.1 mL, 37.7 mmol). After 30 minutes the temperature was adjusted to −20° C. and maintained for 1.5 hour. The temperature of the dark brown solution was lowered to −78° C. and but-4-yne (1.5 g, 14.9 mmol) was added neat. After 1 hour, the temperature was raised to −60° C. for 1.5 hour and the solution was then stored at −20° C. overnight. The reaction mixture was poured onto water, the layers separated, and the aqueous layer was back-extracted with methylene chloride (2×50 mL). The combined organic extracts were washed with brine, dried (MgSO$_4$) and the solvents evaporated at reduced pressure to give the product as an oil.

2-(5-Diethylaminopent-3-ynyl)-2-phenyl-1,3-dithiane Oxalate.

Diethylamine (158 μL, 1.53 mmol), 46 mg (1.53 mmol) of paraformaldehyde and 8 mg of Cu(II)OAc were mixed with 0.5 mL dioxane and warmed to 58° C. for 1.2 hours. 2-(But-3-ynyl)-2-phenyl-1,3-dithiane (380 mg, 1.53 mmol) was added in 1 mL of dioxane and the temperature raised to 85° C. where it was kept overnight. The cooled reaction mixture was poured onto 3 mL of 10% KOH, 40 mL of ether was added and the layers separated. The organics were washed with water (3×20 mL), the aqueous fractions back extracted with methylene chloride (3×10 mL) and the combined organics washed with brine, dried (MgSO$_4$), and the solvents evaporated at reduced pressure. The residue was applied to two preparative TLC plates (silica, 2 mm×20×20 cm, 92:5:3, hexane:EtAc:Et$_3$N) Rf (0.17–0.3) to give 0.38 g (75%) of product. Analytical TLC (silica, 92:5:3, hexane:EtAc:Et$_3$N) Rf. 0.16; IR (neat) 1486(w), 1457(sh), 1442(s), 1421(sh), 1380(w) 1324, 1277, 763, 732, 704(s) cm$^{-1}$; $^1$H NMR (CDCl$_3$) δ 1.02 (t, J=7.2 Hz, 6H), 1.82–1.98 (m, 2H), 2.1–2.2 (m, 2H), 2.2–2.32 (m, 2H), 2.47 (q, J=7.2 Hz, 4H), 3.30 (t, J=2.1 Hz, 2H), 7.2–7.42 (m, 3H), 7.85–7.9 (m, 2H). The oil was converted into its oxalate and recrystalized from THF to give the analytical sample, mp 126°–127° C.

Analysis calcd. for C$_{19}$H$_{27}$NS$_2$−C$_2$H$_2$O$_4$:C, 59.53; H, 6.90; N, 3.32; S, 15.14. Found: C, 59.48; H, 6.94; N, 3.29; S, 15.21.

2-[5-(2-Phenylethylmethylaminopent-3-ynyl)]-2-phenyl-1,3-dithiane oxalate, mp 126°–127° C., was also prepared by this general procedure utilizing 2-phenylethylmethylamine in the Mannich condensation.

EXAMPLE V 2-(Prop-2-ynyl-3-trimethylsilyl)-2-phenyl-1,3-dithiane.

To a solution of 2-phenyl-1,3-dithiane (5.0 g, 25.5 mmol) dissolved in tetrahydrofuran (50 mL) under argon atmosphere at −40° C. was added dropwise 2.5M n-butyllithium (12.2 mL, 30.6 mmol). The solution was stirred for 2.5 hours and trimethyl(3-chloro-1-propynyl)silane (4.0 g, 27.6 mmol) was added neat. The solution was stirred at −40° C. for 2 hours and then allowed to warm to room temperature overnight. Water (50 mL) was added, the layers were separated, and the aqueous layer was back-extracted with methylene chloride (2×15 mL). The combined organic extracts were washed with brine, dried (MgSO$_4$) and evaporated under reduced pressure to afford an oil which was chromatographed on silica (50 g) eluting with hexane to give 6.5 g (83%) of product.

2-(Prop-2-ynyl)-2-phenyl-1,3-dithiane.

2-(Prop-2-ynyl-3-trimethylsilyl)-2-phenyl-1,3-dithiane (6.5 g, 21.2 mmol) and tetrabutylammonium fluoride (8.0 g, 25 mmol) were stirred in tetrahydrofuran at room temperature overnight. The reaction mixture was poured onto water (60 mL), the layers separated, and the aqueous layer was back-extracted with methylene chloride (3×25 mL). The combined organic extracts were washed with brine, dried (MgSO$_4$), and evaporated under reduced pressure to give a dark solid. The solid was chromatographed on silica (50 g, 9:1, hexane:methylene chloride) to give the product as a colorless solid. TLC (silica, 9:1, hexane:methylene chloride) Rf: 0.07. $^1$H NMR (CDCl$_3$) δ: 1.92–201 (m, 2H), 2.08 (t, J=2.6 Hz, 1H), 2.68–2.82 (m, 4H), 2.99 (d, J=2.7 Hz, 2H), 7.25–7.43 (m, 3H), 7.97 (dd, J=0.8 Hz, J=8.3 Hz, 2H) ppm.

2-(4-Dipropylaminobut-2-ynyl)-2-phenyl-1,3-dithiane, Oxalate.

Di-n-propylamine (0.30 g, 2.99 mmol), 90 mg of (2.90 mmol) paraformaldehyde and 16 mg of Cu(II)AcO were mixed with 0.75 mL of dioxane and warmed to 58° C. for 1.5 hours. 2-(Prop-2-ynyl)-2-phenyl-1,3-dithiane (0.7 g, 2.99 mmol) was added and the temperature raised to 87° C. where it was kept overnight. The cooled reaction mixture was stirred with 3 mL of 10% KOH and filtered thru Celite, which was washed with 50 mL of ether. The organics were washed with water (3×15 mL), the aqueous fractions back extracted with methylene chloride (3×10 mL) and the combined organics washed with brine, dried (MgSO$_4$), and evaporated at reduced pressure. The residue was applied to two preparative tlc plates (silica, 2 mm×20×20 cm, 92:5:3, hexane:EtAc:Et$_3$N) to give 0.61 g (59%) of product. Analytical TLC (silica, 92:5:3, hexane:EtAc:Et$_3$N) Rf.16; IR (neat) 1491, 1546, 1447, 1421, 1324, 1275, 1087, 1036, 753 707 cm$^{-1}$. $^1$H NMR (CDCl$_3$) δ 0.99 (t, J=7.2 Hz, 6H), 1.9–2.0 (m, 2H), 2.42 (q, J=7.2 Hz, 4H), 2.64–2.78 (m, 4H), 2.97 (s, 2H, 3.32 (s, 2H), 7.25–7.4 (m, 3H), 7.92–7.99 (m, 2H). The oil was converted into its oxalate and recrystallized from THF/ether to give the analytical sample as a colorless powder, mp 113°–114° C.

Analysis calcd. for C$_{20}$H$_{29}$NS$_2$+C$_2$H$_2$O$_4$:C, 60,37; H, 7.14; N, 3.21; S, 14.65. Found: C, 60:43; H, 7.19; N, 3.20; S, 14.63.

Also prepared by this general method were: 2-(4-diethylaminobut-2-ynyl)-2-phenyl-1,3-dithiane oxalate, mp 144°–146° C., and 2-[4-[2-(3,4-dimethoxyphenyl)ethyl]methylaminobut-2-ynyl]-2-phenyl-1,3-dithiane oxalate, mp 144°–146° C.

EXAMPLE VI 6-(Oxacyclohex-2-yloxy)hex-1-yne.

To a stirred mixture of hex-6-yn-1-ol (35 g, 360 mmol) and 3,4-dihydro-2H-pyran (32.5 mL, 360 mmol) dissolved in methylene chloride (100 mL) was added pyridinium p-toluenesulfonate (0.5 g). After stirring overnight at room temperature the mixture was extracted with water, washed with brine and dried (MgSO$_4$). Evaporation of the solvent under reduced pressure gave a residue which was Kugelrohr distilled (b.p. 100° C., 0.1 mm Hg) to afford 60.2 g (92%) of the product. $^1$H NMR (CDCl$_3$) δ 1.51–1.85 (m, 10H), 1.96 (t, 1H), 2.20–2.26 (m, 2H), 3.39–3.52 (m, 2H), 3.72–3.85 (m, 2H) 4.58 (t, 1H) ppm.

1-Trimethylsilyl [6-(oxacyclohex-2-yloxy)hex-1-yne.

To a stirred solution of 6-(oxacyclohex-2-yloxy)hex-1-yne (60.2 g, 330 mmol) in tetrahydrofuran (250 mL) at −78° C. under argon atmosphere was added 1.4M methyllithium (280 mL, 390 mmol) dropwise. After stirring 1 hour trimethylsilyl chloride (49.2 mL, 390 mmol) was added and the solution was allowed to warm to room temperature overnight. Water (150 mL) was added, the layers were separated, and the organic extract was washed with brine, dried (MgSO$_4$), and evaporated under reduced pressure to give the product as a liquid. The residue was Kugelrohr distilled (90° C. oven, 0.1 mm Hg) to afford 76 g (83%) of the purified product.

1-Trimethylsilylhex-1-yn-6-ol.

1-Trimethylsilyl[6-(oxacyclohex-2-yloxy)]hex-1-yne (76 g, 300 mmol) and pyridinium p-toluenesulfonate (0.05 g) were heated at reflux in methanol (200 mL). After cooling the solvent was removed under reduced pressure, the residue was dissolved in methylene chloride and washed with water, brine and dried (MgSO$_4$). Evaporation of the solvent under reduced pressure afforded a residue which was distilled (b.p. 96° C., 3 mm Hg) to give 37.6 g (64%) of the product.

1-Trimethylsilyl-6-bromohex-1-yne.

To a mixture of 1-trimethylsilyl(hex-1-yn-6-ol) (32.6 g, 190 mmol) and pyridine (0.38 mL) dissolved in diethyl ether (100 mL) was added slowly phosphorus tribromide (7.1 mL, 75 mmol) in diethyl ether (20 mL). Upon addition a precipitate formed and the heterogeneous solution was stirred at room temperature overnight. The mixture was then heated at reflux for 2.5 hours and, upon cooling, was poured onto ice, washed with water, sodium bicarbonate solution, brine and dried (MgSO$_4$). Evaporation of solvent under reduced pressure gave a residue which was distilled (b.p. 80° C., 3.5 mm Hg) to give 22 g (50%) of product. $^1$H NMR (CDCl$_3$) δ: 0.14 (s, 9H), 1.64–1.72 (quintet, 2H), 1.91–2.02 (quintet, 2H), 2.27 (t, 2H), 3.44 (t, 2H) ppm.

2-[(Hex-5-ynyl)-3-trimethylsilyl]-1,3-dithiane.

To a solution of dithiane (2.5 g, 20.8 mmol) in tetrahydrofuran (20 mL) at −40° C. under argon atmosphere was added 2.5M n-butyllithium (10 mL, 25 mmol). After 30 minutes the temperature was raised to −20° C. and maintained for 1.5 hours. The temperature was then lowered to −40° C. and 1-trimethylsilyl-6-bromohex-1-yne (5.3 g, 22.9 mmol) was added. The solution was stirred for 1.5 hours and stored at −15° C. overnight.

The mixture was poured onto water, the aqueous layer was extracted with methylene chloride (2×15 mL) and the combined organic extracts were washed with brine and dried (MgSO$_4$). Evaporation of solvent under reduced pressure afforded the purified products as an oil. $^1$H NMR (CDCl$_3$) δ: 0.14 (s, 9H), 1.54–1.63 (m, 4H), 1.73–1.85 (m, 3H), 2.09–2.13 (m, 1H), 2.22 (t, 2H), 2.80–2.92 (m, 4H), 4.05 (t, 1H) ppm.

2-(Hex-5-ynyl)-1,3-dithiane.

A mixture of 2-[(hex-5-ynyl)-3-trimethylsilyl]-1,3-dithiane (8.9 g, 33 mmol) and tetrabutylammonium fluoride (11.3 g, 33 mmol) was heated at reflux in methanol (50 mL) for 1 hour. Upon cooling, the solvent was removed under reduced pressure and the residue was partitioned between diethyl ether and water. The organic extract was washed with brine, dried (MgSO$_4$), and evaporated under reduced pressure. The residue was chromatographed on silica (hexane:ethyl acetate, 99:1, 98:2, and 9:1) to give 5.6 g (84%) of product. $^1$H NMR (CDCl$_3$) δ: 1.53–1.66 (m, 4H), 1.70–1.90 (m, 3H), 1.95 (t, 1H), 2.08–2.23 (m, 3H), 2.82–2.95 (m, 4H), 4.05 (t, 1H) ppm. IR (film): 3291, 2116, 1457, 1421, 1275, 1244, 1182, 907, 635 cm$^{-1}$.

2-(7-Diethylaminohept-5-ynyl)-1,3-dithiane.

Diethylamine (1.29 mL, 14.5 mmol), paraformaldehyde (435 mg, 14.5 mmol) and 70 mg of Cu(II) acetate were mixed with 3.5 mL of dioxane and the mixture was stirred at 55°–60° C. for 45 minutes. 2-(Hex-5-ynyl)-1,3-dithiane (3.8 g, 14.5 mmol) was added and the temperature of the stirred mixture was increased to 85°–90° C. where it was maintained for 16 hours. After the stirred mixture was cooled to 20° C., 10 mL of a 10% aqueous solution of KOH was added. The mixture was filtered through Celite and the filter cake was washed with 50 mL of ether. The organic layer was separated, washed with water (2×10 mL) and the aqueous layer was extracted with methylene chloride (2×10 mL). The combined organic extracts were washed with brine, dried over MgSO$_4$ and concentrated at reduced pressure. The residue was chromatographed on 100 g of silica (9:1, hexane:ethyl acetate, then 8:2 and 6:4 hexane:ethyl acetate) to give 2.3 g (56%) of a liquid. Analytical TLC (Silica, 92:5:3, hexane:ethyl acetate:triethylamine) gave a single spot, Rf. 0.19. IR (neat) 1460, 1427, 1378, 1326, 1277, 1198, 1123, 1092, 1069, 789, 768 cm$^{-1}$. $^1$H NMR (CDCl$_3$) δ1.06 (t, J=7.2 Hz, 6H), 1.48–1.68 (m, 4H), 1.72–1.94 (m, 3H), 2.08–2.24 (m, 3H), 2.53 (q, J=7.2 Hz, 4H), 2.79–2.95 (m, 4H), 3.38 (t, J=2.1 Hz, 2H), 4.05 (t, J=6.9 Hz, 1H).

Anal. calcd. for C$_{15}$H$_{27}$NS$_2$: C, 63.09; H, 9.53; N, 4.93; S, 22.45. Found: C, 63.16; H, 9.56; N, 4.87; S, 22.40.

2-(7-Diethylaminohept-5-ynyl)-2-(9-hydroxy-9H-xanthen-9-yl)-1,3-dithiane Oxalate.

A solution of 2-(7-diethylaminohept-5-ynyl)-1,3-dithiane (1.32 g, 4.6 mmol) in 40 mL of tetrahydrofuran was stirred at −40° C. under argon and 1.8 mL of a 2.5M solution of n-butyllithium in hexane (4.6 mmol) was added dropwise. After 10 minutes the temperature was adjusted to −20° C. The mixture was stirred for 35 minutes at −20° C. and then 0.9 g (4.6 mmol) of xanthone was added in one portion. After 16 hours at −20° C. the reaction mixture was poured into 200 mL of water. The layers were separated, the aqueous layer was extracted with methylene chloride (3×10 mL), and the organic layers were combined, washed with brine, dried (MgSO$_4$), and concentrated. The residue was applied to two preparative TLC plates (silica, 20×20 cm×2 mm, 1:1, hexane:ethyl acetate) to give 900 mg of a mixture of product and starting material which was applied to three preparative TLC plates (silica, 20×20 cm×2 mm, 92:5:3, Hexane:EtAc:Et$_3$N) to give 200 mg (16%) of product that was converted into its oxalate and recrystallized from THF-ether to give the analytical sample, mp 181°–182° C. Analytical TLC (silica, 92:5:3, hexane:ethyl acetate:triethylamine) Rf.08; IR(KBr) 3414(b), 2692(b), 1738(b), 1648(b), 1599, 1473, 1447, 1277, 1239, 760, 704 cm$^{-1}$ $^1$H NMR (CDCl$_3$) δ1.00 (t, J=7.2 Hz, 6H), 1.22–1.36 (m, 4H), 1.49–1.62 (m, 2H), 1.65–1.82 (m, 1H), 1.84–1.98 (m, 1H), 2.0–2.09 (m, 2H), 2.47 (q, J=7.2 Hz, 4H), 2.50–2.60 (m, 2H), 2.89–3.02 (m, 2H), 3.29 (s, 2H), 3.6 (bs, 1H), 7.09–7.22 (m, 4H), 7.35 (dt, J=1.3 Hz, J=7.6 Hz, 2H), 7.91 (dd, J=1.3 Hz, J=7.8 Hz, 2H).

Anal. calcd. for C$_{28}$H$_{35}$NO$_2$S$_2$·C$_2$H$_2$O$_4$: C, 63.01; H, 6.52; N, 2.46; S, 11.21. Found: C, 62.85; H, 6.63; N, 2.42; S, 11.15.

Example VII

Pent-4-ynal.

To a solution of oxalyl chloride (9.12 mL, 104.6 mmol) in methylene chloride (200 mL) at −78° C. was added dimethylsulfoxide (14.8 mL, 209.2 mmol) dissolved in methylene chloride (40 mL) over 20 minutes. The reaction solution was kept under a positive pressure of argon until workup. The reaction mixture was stirred for an additional 30 minutes when pent-4-yn-1-ol (8.00 g, 95.1 mmol) dissolved in methylene chloride (80 mL) was added over 10 minutes. Stirring was continued for an additional 60 minutes. Triethylamine (66.2 mL, 475.5 mmol) was added at −78° C. and the reaction mixture was stirred for 60 minutes and then allowed to warm to 10° C. over an additional hour. Water (200 mL) was added and the two layers were separated. The aqueous layer was acidified with 1% hydrochloric acid solution (saturated with NaCl) and then back-extracted with methylene chloride (3×100 mL). The combined organic layers were washed with 1% hydrochloric acid (in saturated brine solution, 6×100 mL) and 5% sodium bicarbonate solution (2×50 mL). The aqueous extracts were back-extracted with methylene chloride (2×100 mL). The combined organic extracts were washed with brine (2×50 mL) and dried (MgSO$_4$). The solvent was removed by rotary evaporation (30° C. water bath) to give 7.18 g (92%) of pent-4-ynal as a yellow oil. $^1$H NMR (CDCl$_3$) δ: 9.8 (s, 1H), 2.8–2.3 (m, 4H), 2.0–1.9 (t, 1H); IR (neat): 3296(s), 2926, 2848, 1725(s) cm$^{-1}$; TLC (silica gel, 90% hexane:10% ethyl acetate) Rf=0.43.

1-Hydroxy-1-phenylpent-4-yne.

To an ice-cold solution of 3.0M phenylmagnesium bromide (100 mL, 300 mmol) under argon atmosphere was added dropwise pent-4-yn-1-ol (10 g, 120 mmol) in diethyl ether (20 mL). After stirring for 3 hours the solution was slowly added to an ice-cold solution of dilute ammonium chloride. 6N Hydrochloric acid was added to break up the gel and the layers were separated. The aqueous extract was washed with diethyl ether (3×50 mL) and the combined organic extracts were washed with brine and dried (MgSO$_4$). The solvent was removed by rotary evaporation under reduced pressure to give 17 g of the crude product which was Kugelrohr distilled to afford 11.1 g (58%) of the purified product. $^1$H NMR (CDCl$_3$) δ: 1.82–1.95 (m, 2H), 1.98 (t, 1H), 2.20–2.35 (m, 2H), 2.40 (s, 1H), 4.80–4.85 (m, 1H), 7.30–7.38 (m, 5H) ppm.

But-3-ynyl phenyl ketone.

To a solution of oxalyl chloride (7.0 mL, 76.6 mmol) in methylene chloride (200 mL) under argon atmosphere at −78° C. was added dropwise dimethylsulfoxide (11.9 mL, 152 mmol). After stirring for 15 minutes 1-hydroxy-1-phenylpent-4-yne (11.14 g, 69.6 mmol) in methylene chloride (20 mL) was added dropwise. After stirring at −78° C. for 1 hour triethylamine (48 mL, 340 mmol) was added and the orange reaction mixture was allowed to warm to room temperature. Water (100 mL) was added, the layers separated, and the organic extract was washed with 1% hydrochloric acid solution (4×100 mL), saturated sodium bicarbonate solution, brine, and dried (MgSO$_4$). Evaporation of solvent under reduced pressure gave a solid which was recrystallized from petroleum ether to afford 5.25 g product. The mother liquors were distilled by Kugelrohr (80° C., 0.1 mm Hg) to give an additional 8.3 g (75%) of product. $^1$H NMR (CDCl$_3$) δ: 1.99 (t, J=2.69 Hz, 1H), 2.63 (t, J=7.21 Hz, 1H), 2.64 (t, J=6.17 Hz, 1H), 3.25 (t, J=6.23 Hz, 1H), 3.26 (t, J=7.20 Hz, 1H), 7.44–7.58 (m, 3H), 7.96–7.99 (m, 2H) ppm.

2-(1-Hydroxy-1-phenylpent-4-ynyl)-1,3-dithiane.

1,3-Dithiane (3.8 g, 31.6 mmol) was stirred in 120 mL of tetrahydrofuran at −40° C. under argon and 13.2 g (33 mmol) of 2.5M n-BuLi in hexane was added. After 10 minutes the temperature was adjusted to −20° C. and 1.25 hours later 2.27 g (14.36 mmol) of but-3-ynyl phenyl ketone was added as a solid. Stirring was continued for 20 minutes before placing in a freezer at −20° C. for 20 hours. The mixture was then poured onto water, the layers were separated, and the aqueous portion extracted with methylene chloride (3×30 mL). The combined organics were washed with brine, dried (MgSO$_4$) and solvents evaporated at reduced pressure. The residue was chromatographed on 75 g silica (98:2, hexane:EtAc, then 4%, 10%, and 20% EtAc) to give 3.0 g (75%) of product.

2-(1-Phenyl-1-trimethylsilyloxypent-4-ynyl)-1,3dithiane.

2-(1-Hydroxy-1-phenylpent-4-ynyl)-1,3 -dithiane (1.7 g 6.1 mmol) and 1.2 g (15 mmol) of imidazole was stirred in 25 mL of methylene chloride and 0.9 mL (15 mmol) of chlorotrimethylsilane was added. The mixture was stirred overnight when it was poured onto 20 mL of 10% aqueous K$_2$CO$_3$. The organics were washed with brine, dried (Na$_2$SO$_4$) and concentrated at reduced pressure. The residue was mixed with Celite and chromatographed on 110 g of silica (99:1, hexane:ethyl acetate, then 2% ethyl acetate) to give 2.14 g (90%) of a product that crystallized upon concentration at reduced pressure. Analytical TLC (silica, 9:2, hexane:ethyl acetate) Rf0.56; $^1$H NMR (CDCl$_3$) δ1.65–2.05 (m, 5H), 2.05–2.2 (m, 1H), 2.28–2.4 (m, 1H), 2.45–2.6 (m, 1H), 2.7–2.87 (m, 4H), 4.37 (s, 1H), 7.25–7.4 (m, 3H), 7.42–7.5 (m, 2H).

2-[6-[2-(3,4-Dimethoxyphenyl)ethyl]methylaminohex-4-ynyl]-1-trimethylsilyloxy-1-phenyl-1,3-dithiane.

Paraformaldehyde (86 mg, 2.86 mmol), 0.415 g (2.86 mmol) of N-methylphenylethylamine, and 12 mg copper(II) acetate were heated in 1.8 mL of dioxane at 58°–60° C. for 1 hour when 1.0 g (2.86 mmol) 2-(1-trimethylsilyloxy-1-phenyl(pent-4-ynyl)-1,3-dithiane (from corresponding alcohol and trimethylsilyl chloride) was added. The temperature was adjusted to 87° C. where it was kept overnight. Upon cooling the mixture was poured onto 5 mL of 10% KOH and filtered through Celite which was subsequently washed with 50 mL of ether. The organics were separated and washed with water (3×20 mL), brine, and dried (MgSO$_4$) before evaporation at reduced pressure. The residue was chromatographed on 50 g silica (8:2, hexane:ethyl acetate, 8:2:0.1, hexane:ethyl acetate:triethylamine) to give 1.3 g (91%) of product as a slightly yellow oil. Analytical TLC (1:1, ethyl acetate:hexane) Rf0.55; IR (neat) 3500(b), 1591(w), 1519(s), 1463, 1419, 1259, 1139, 1033, 864, 835, 781, 763 cm$^{-1}$; $^1$H NMR (CDCl$_3$) δ0.40 (s, 9H), 1.7–1.85 (m, 1H), 1.85–2.05 (m, 2H), 2.18–2.3 (m, 1H), 2.35–2.5 (m, 1H), 2.40 (s, 3H), 2.5–2.65 (m, 1H), 2.7–2.9 (m, 8H), 3.39 (s, 2H), 4,44 (s, 1H), 7.2–7.45 (m, 8H), 7.5–7.55 (m, 2H).

Anal. calcd. for C$_{30}$H$_{43}$O$_3$S$_2$Si: 3, 64.58; H, 7.77; N. 252; S, 11.49. Found: C, 64.66; H, 7.92; N, 2.48; S, 11.22.

Also prepared by this general synthetic sequence were: 2-(6-diethylamino-1-hydroxy-1-phenylhex-4-ynyl)-1,3-dithiane oxalate, mp 139.5°–144° C., 2-[6-(2-phenylethyl)methylamino-1-hydroxy-1-phenyl-hex-4-ynyl]-1,3-dithiane oxalate hemihydrate, mp 70.5°–75° C., and 2[6-[2-(3,4-dimethoxyphenyl)ethyl]methylamino-1-hydroxy-1-phenylhex-4-ynyl]-1,3-dithiane, a liquid purified by chromatography.

Example VIII

Calcium Channel Antagonist Activity in Guinea-Pig Isolated Ileal Smooth Muscle.

Male albino guinea-pigs are sacrificed by stunning and exsanguination. The abdominal cavity is opened and the small intestine is removed, with about 10 cm of the terminal ileum being discarded. The tissue is placed in a dish containing Tyrode's solution (composition, mM: CaCl 136.90; KCl 2.68; NaHCO$_3$ 11.90; NaH$_2$PO$_4$ 0.36; MgCl$_2$ 0.98; CaCl$_2$ 1.77; dextrose 5.55), and cut into three to four segments. A glass rod (6 mm diameter) is carefully inserted into the lumen of each segment, and excess connective tissue or fat is removed. The longitudinal smooth muscle is carefully separated from the underlying circular muscle layer by gently stroking a moist cotton swab on a tangent to shallow, longitudinal incisions made parallel to the mesenteric attachment. Using gentle traction, and taking care to keep the segment moist at all times, the preparation is stripped from the remaining length of the ileal segment (Paton & Zar, J. Physiol. 194, 13; 1968).

Each preparation is suspended in a 10 mL jacketed glass tissue bath containing Tyrode's solution maintained at 37° C. and gassed with 5% CO$_2$ in O$_2$. The preparation is attached by silk thread to a force-displacement transducer. Tension changes are recorded isometricaly and displayed on a chart recorder. The initial resting tension is adjusted to 0.5 g and the preparation equilibrated for 55 minutes prior to experimentation. At the end of this period, the bathing solution is replaced with Ca$^{2+}$-free Tyrode's solution. This solution is prepared by omitting CaCl$_2$. The preparation is washed four times in Ca$^{2+}$-free Tyrode 's to remove any Ca$^{2+}$ remaining in the bath, and allowed to equilibrate for a further 20 minutes.

Experimental protocol.

Concentration-response curves to CaCl$_2$ are obtained using the following procedure. Preparations are exposed to a depolarizing concentration of KCl (80 mM) for 6 minutes. At the end of this period CaCl$_2$ is added to the bath cumulatively in the concentration range 0.2–8.0 mM. Successive additions of each Ca$^{2+}$ concentration are carried out only when the previous response has reached a plateau. When the maximum response has been attained the bath is again washed (five times) with Ca²⁺-free buffer, and the preparation re-equilibrated for approximately 15 minutes. A second $Ca^{2+}$ concentration-response curve is then obtained in the same manner. This second curve serves as control for that tissue.

Further curves are obtained in the presence of increasing concentrations of the test drugs. Where appropriate, the test drug is added to the bath immediately following addition of KCl, and 6 minutes later the concentration-response curve to $Ca^{2+}$ is obtained. Each test preparation is exposed to three different concentrations of a test drug.

For each ileal preparation, the control $EC_{50}$ for $Ca^{2+}$ (the concentration producing 50% of the maximum response) is determined from the control concentration-response curve. Calcium blocking activity is defined as a Kb value (the concentration producing a two-fold dextral shift in the control curve), calculated from $EC_{50}$ ratios in the absence and presence of test drugs.

The results of testing of the novel compounds described herein are as follows:

| Compound | Calcium antagonist Kb, mM |
|---|---|
| 2-[5-(4-Methylpiperazinyl)pent-3-ynyl]-2-(9-hydroxy-9H—xanthen-9-yl)-1,3-dithiane Dioxalate | 0.488 ± 0.03 |
| 2-[5-(4-Methylpiperazinyl)pent-3-ynyl]-1,3-dithiane Dioxalate | >10.0 |
| 2-[5-[4-(2-Hydroxyethyl)piperazinyl]-pent-3-ynyl]-1,3-dithiane Dioxalate | >10.0 |
| 2-[5-[2-(3,4-Dimethoxyphenyl)ethyl]-methylaminopent-3-ynyl]-1,3-dithiane Oxalate | 2.22 ± 0.07 |
| 2-[5-(4-Phenylbutyl)methylamino-pent-3-ynyl]-1,3-dithiane Oxalate | 3.43 ± 0.83 |
| 2-[5-(4-Phenylbutyl)methylaminopent-3-ynyl]-2-(9-hydroxy-9H—xanthen-9-yl)-1,3-dithiane | — |
| 2-[5-(4-Phenylbutyl)methylaminopent-3-ynyl]-2-(9-hydroxy-9H—thioxanthen-9-yl)-1,3-dithiane | — |
| 2-(5-Diethylaminopent-3-ynyl)-2-(5-hydroxy-5H—dibenzo[a,d]cyclo-hepten-5-yl)-1,3-dithiane Oxalate | 0.30 |
| 2-[5-(3-Phenylpropyl)ethylamino-pent-3-ynyl]-2-(9-hydroxy-9H—xanthen-9-yl)-1,3-dithiane | — |
| 2-(5-Diethylaminopent-3-ynyl)-2-(9-hydroxy-9H—xanthen-9-yl)-1,3-dithiane | 0.156 ± 0.03 |
| 2-(5-Diethylaminopent-3-ynyl)-2-(alpha-cyclohexyl-alpha-hydroxybenzyl)-1,3-dithiane Hemioxalate | 1.140 ± 0.021 |
| 2-(5-Diethylaminopent-3-ynyl)-2-(alpha-cyclopentyl-alpha-hydroxy-benzyl)-1,3-dithiane Oxalate | 0.500 |
| 2-(5-Diethylaminopent-3-ynyl)-1,3-dithiane Oxalate | >10.0 |
| 2-(5-Diethylaminopent-3-ynyl)-2-(alpha-hydroxy-alpha-phenylbenzyl)-1,3-dithiane Oxalate | 0.98 ± 0.16 |
| 2-(5-Diethylaminopent-3-ynyl)-2-(1-hydroxy-1,2,3,4-tetrahydro-1-naphthyl)-1,3-dithiane Hemioxalate | 0.83 ± 0.02 |
| 2-[5-(2-Phenylethyl)methylamino-pent-3-ynyl]-2-(alpha-cyclohexyl-alpha-hydroxybenzyl)-1,3-dithiane Oxalate | 3.75 ± 1.25 |
| 2-(5-Diethylaminopent-3-ynyl)-2-(alpha-hydroxy-alpha-methylbenzyl)-1,3-dithiane | 2.51 ± 0.40 |
| 2-[5-(2-Phenylethyl)methylaminopent-3-ynyl]-2-(alpha-hydroxy-alpha-phenylbenzyl)-1,3-dithiane Oxalate Hemihydrate | 2.65 ± 1.21 |
| 2-[5-(2-Phenylethyl)methylaminopent-3-ynyl]-1,3-dithiane Oxalate | 2.27 ± 0.73 |
| 2-(5-Diethylaminopent-3-ynyl)-2-benzyl-1,3-dithiane Oxalate | 1.960 ± 0.40 |
| 2-(5-Diethylaminopent-3-ynyl)-2-benzhydryl-1,3-dithiane Oxalate Hydrate | 0.500 |
| 2-(5-Piperidinylpent-3-ynyl)-2-(9-hydroxy-9H—xanthen-9-yl)-1,3-dithiane | 0.399 ± 0.04 |
| 2-(5-Ethylmethylaminopent-3-ynyl)-1,3-dithiane Oxalate | >10.0 |
| 2-(5-Piperidinylpent-3-ynyl)-1,3-dithiane Oxalate | >10.0 |
| 2-(5-Dimethylaminopent-3-ynyl)-1,3-dithane Oxalate | >10.0 |
| 2-(5-Pyrrolidinylpent-3-ynyl)-1,3-dithiane Oxalate | >10.0 |
| 2-[5-(Benzylmethylaminopent-3-ynyl]-2-(alpha-hydroxy-alpha-phenyl-benzyl)-1,3-dithiane Oxalate Hemihydrate | 3.17 ± 0.76 |
| 2-[5-(Benzylmethylaminopent-3-ynyl]-1,3-dithiane Oxalate | 8.02 ± 2.74 |
| 2-[5-(3-Phenylpropyl)methylaminopent-3-ynyl]-1,3-dithiane Oxalate | 2.98 ± 0.59 |
| 2-[5-(1-Naphthylmethyl)methylaminopent-3-ynyl]-1,3-dithiane Oxalate | >10.0 |
| 2-[5-(2-Naphthylmethyl)methylaminopent-3-ynyl]-1,3-dithiane Oxalate | 8.33 ± 2.04 |
| 2-[5-(2-Naphthylethyl)methylaminopent-3-ynyl]-1,3-dithiane Oxalate | 1.52 ± 0.13 |
| 2-[5-(2-Naphthylethyl)methylamino-pent-3-ynyl]-1,3-dithiane Oxalate | 4.73 ± 1.39 |
| 2-[5-(3-Phenylpropyl)methylaminopent-3-ynyl]-2-(9-hydroxy-9H—phenylbenzyl)-1,3-dithiane Oxalate | 1.63 ± 0.88 |
| 2-[5-(3-Phenylpropyl)methylaminopent-3-ynyl]-2-(9-hydroxy-9H—xanthen-9-yl)-1,3-dithiane | 3.09 ± 0.99 |
| 2-[5-(3-Phenylpropyl)methylaminopent-3-ynyl]-2-(9-hydroxy-9H—thioxanthen-9-yl)-1,3-dithiane | 4.16 ± 0.86 |
| 2-(5-Dimethylaminopent-3-ynyl)-2-(9-hydroxy-9H—xanthen-9-yl)-1,3-dithiane | 1.15 ± 0.20 |
| 2-[5-(3-Phenylpropyl)methylaminopent-3-ynyl]-2-(2-chloro-9-hydroxy-9H—thioxanthen-9-yl)]-1,3-dithiane Hemioxalate | >7.00 |
| 2-(5-Dimethylaminopent-3-ynyl)-2-(2-chloro-9-hydroxy-9H—thioxanthen-9-yl)-1,3-dithiane | 2.33 ± 0.18 |
| 2-(5-Dimethylaminopent-3-ynyl)-2-(9-hydroxy-9H—thioxanthen-9-yl)-1,3-dithiane | 0.68 ± 0.13 |
| 2-(5-Dimethylaminopent-3-ynyl)-2-(9-hydroxy-9H—fluoren-9-yl)-1,3-dithiane | 1.81 ± 0.39 |
| 2-(5-Ethylmethylaminopent-3-ynyl)-2-(9-hydroxy-9H—xanthen-9-yl)-1,3-dithiane | 1.51 ± 0.53 |
| 2-(5-Ethylmethylaminopent-3-ynyl)-2-(9-hydroxy-9H—thioxanthen-9-yl)-1,3-dithiane | 0.57 ± 0.12 |
| 2-(5-Ethylmethylaminopent-3-ynyl)-2-(2-chloro-9-hydroxy-9H—thioxanthen-9-yl)-1,3-dithiane | 2.53 ± 1.03 |
| 2-(5-Diethylaminopent-3-ynyl)-2-(9-hydroxy-9H—thioxanthen-9-yl)-1,3-dithiane Oxalate | 0.125 ± 0.018 |
| 2-(5-Ethylmethylaminopent-3-ynyl)-2-(9-hydroxy-9H—fluoren-9-yl)-1,3-dithiane | 1.23 ± 0.47 |

| Compound | Calcium antagonist Kb, mM |
|---|---|
| 2-(5-Diethylaminopent-3-ynyl)-2-(9-hydroxy-9H—fluoren-9-yl)-1,3-dithiane | 0.50 ± 0.10 |
| 2-(5-Diethylaminopent-3-ynyl)-2-(2-chloro-9-hydroxy-9H—thioxanthen-9-yl)-1,3-dithiane Oxalate | 0.33 ± 0.05 |
| 2-(5-Piperidinylpent-3-ynyl)-2-(9-hydroxy-9H—thioxanthen-9-yl)-1,3-dithiane | 3.66 ± 2.04 |
| 2-(5-Piperidinylpent-3-ynyl)-2-(2-chloro-9-hydroxy-9H—thioxanthen-9-yl)-1,3-dithiane | 6.09 ± 1.56 |
| 2-(5-Piperidinylpent-3-ynyl)-2-(9-hydroxy-9H—fluoren-9-yl)-1,3-dithiane | 1.00 ± 0.07 |
| 2-(5-Diethylaminopent-3-ynyl)-2-(4-hydroxy-4H—chromanyl)-1,3-dithiane | 1.94 ± 0.21 |
| 2-(5-Diethylaminopent-3-ynyl)-2-(5-hydroxy-10,11-dihydro-5H—dibenzo[a,d]cyclohepten-5-yl)-1,3-dithiane Oxalate Hemihydrate | — |
| 2-(6-Diethylaminohex-4-ynyl)-2-(9-hydroxy-9H—Xanthen-9-yl)-1,3-dithiane | 0.17 ± 0.02 |
| 2-(6-Benzylmethylaminohex-4-ynyl)-1,3-dithiane Oxalate | 4.45 ± 0.16 |
| 2-[6-(2-Phenylethyl)methylaminohex-4-ynyl]-1,3-dithiane Oxalate | 4.18 ± 1.54 |
| 2-(6-Diethylaminohex-4-ynyl)-1,3-dithiane Oxalate | >10.0 |
| 2-(6-Diethylaminohex-4-ynyl)-2-(9-hydroxy-9H—fluoren-9-yl)-1,3-dithiane | 0.81 ± 0.22 |
| 2-(6-Dipropylaminohex-4-ynyl)-2-(9-hydroxy-9H—xanthen-9-yl)-1,3-dithiane | 0.47 ± 0.15 |
| 2-(6-Dipropylaminohex-4-ynyl)-2-(9-hydroxy-9H—fluoren-9-yl)-1,3-dithiane | 0.56 ± 0.08 |
| 2-(6-Dipropylaminohex-4-ynyl)-2-(9-hydroxy-9H—thioxanthen-9-yl)-1,3-dithiane | 0.77 ± — |
| 2-(6-Ethylisopropylamino)hex-4-ynyl)-2-(9-hydroxy-9H—xanthen-9-yl)-1,3-dithiane | — |
| 2-(6-Diisopropylamino)hex-4-ynyl)-2-(9-hydroxy-9H—xanthen-9-yl)-1,3-dithiane | — |
| 2-(5-Diethylaminopent-3-ynyl)-2-phenyl-1,3-dithiane Oxalate | 0.90 ± 0.30 |
| 2-[5-(2-Phenylethyl)methylaminopent-3-ynyl]-2-phenyl-1,3-dithiane Oxalate | 1.74 ± 1.08 |
| 2-[4-[2-(3,4-dimethoxyphenyl)ethyl]methylaminobut-2-ynyl]-2-phenyl-1,3-dithiane Oxalate | 1.17 ± 0.35 |
| 2-(4-Diethylaminobut-2-ynyl-2-phenyl-1,3-dithiane Oxalate | 4.27 ± 0.43 |
| 2-(4-Dipropylaminobut-2-ynyl)-2-phenyl-1,3-dithiane Oxalate | 1.01 ± 0.15 |
| 2-(7-Diethylaminohept-5-ynyl)-1,3-dithiane Oxalate | — |
| 2-(6-Diethylamino-1-hydroxy-1-phenylhex-4-ynyl)-1,3-dithiane Oxalate | 6.71 ± 1.45 |
| 2-(7-Diethylaminohept-5-ynyl)-2-(9-hydroxy-9H—xanthen-9-yl)-1,3-dithiane Oxalate | — |
| 2-[6-[2-(3,4-Dimethoxyphenyl)ethyl]methylamino-1-phenyl-1-trimethylsilyloxyhex-4-ynyl]-1,3-dithiane | 0.57 ± .03 |
| 2-[6-(2-Phenylethyl)methylamino-1-hydroxy-1-phenylhex-4-ynyl]-1,3-dithiane Oxalate Hemihydrate | 2.25 ± 0.53 |
| 2-[6-[2-(3,4-Dimethoxyphenyl)ethyl]methylamino-1-hydroxy-1-phenylhex-4-ynyl]-1,3-dithiane | 1.23 ± 0.53 |

Example IX

Inhibition of Ileal Secretion.

This technique involves the measurement of Cl− ion secretion by guinea-pig isolated ileal mucosa, and provides a method for assessing the effect of drugs on intestinal electrolyte and water secretion. Abnormalities in intestinal secretion contribute to diarrhea. Cl− ion secretion in vitro, which is $Ca^{2+}$-dependent, is quantitated as changes in electrical current (Isc) under short-circuited conditions.

Male Hartley guinea-pigs weighing 200–400 g were maintained on a standard laboratory diet with free access to food and water prior to sacrifice by decapitation. An approximately 15 cm segment of proximal ileum was removed and stripped of its underlying longitudinal muscle by blunt dissection. Four adjacent tissues were each mounted as flat sheets between Ussing chambers (two lucite half-chambers, exposed area=0.64 $cm^2$) and bathed on both sides by a physiological salt solution circulated by gas lift, and maintained at a pH of 7.4. The ionic composition in mmol/liter was: $Na+$, 142; $K+$, 5.0; $Cl-$, 123.7; $HCO_3-$, 25; $HPO_4-$, 1.65; $H_2PO_4-$, 0.3.

Electrical measurements were monitored with an automatic voltage clamp (World Precision Instruments, model DVC-1000). Two calomel electrodes with 4% agar Krebs Bicarbonate Ringer bridges were used to measure the transepithelial potential difference (PD) across the isolated mucosa. The spontaneous tissue PD was short-circuited throughout the experiment and the clamp current (Isc) was passed with silver/silver chloride electrodes located on each side of the tissue. The Isc was recorded on a Gould chart recorder.

Tissues were equilibrated for 30 minutes prior to exposure to drugs. Substance P (1 μM), a potent stimulant of mucosal electrolyte secretion, was added to the Ussing chamber in the absence and presence of the test compounds loperamide, verapamil, 2-(5-diethylaminopent-3-ynyl)-2-(9-hydroxy-9H-xanthen-9-yl)-1,3-dithiane or other test compounds. These antagonists, at concentrations of 5 μM, were added to both the serosal and mucosal sides of the tissue 5 minutes prior to the addition of substance P.

The percent inhibition of substance P-induced increase in Isc was as follows: verapamil, 33.5%; loperamide, 36.1%; 2-(5-diethylaminopent-3-ynyl)-2-(9-hydroxy-9H-xanthen-9-yl)-1,3-dithiane, 55.2%.

Example X

Inhibition of Serotonin-Induced Diarrhea in Mice.

Male CF1 mice (20–30 g) were allowed food and water ad libitum prior to the experiments. The mice were weighed and an average weight was used to calculate the amount of drug to be administered. Drugs were prepared in isotonic saline or an appropriate vehicle at varying concentrations and were administered intraperitoneally. Control animals were given vehicles without any test drug. Serotonin was given intraperitoneally (i.p.) in all cases 30 minutes after i.p. administration of test drug. Mice were placed in individual cages containing racks and paper liners with free access to water. Mice were observed after 30 minutes, 60 minutes and 180 minutes and graded for presence or absence of diarrhea. The grading system consisted of positive (+), negative (−) and (±) based on consistency and liquid staining. The $ED_{50}$ (effective dose in 50% of population) was calculated for each test drug using the method of Litchfield-Wilcoxin. In this test the $ED_{50}$ values (95% confidence limits) were 13.3 (5.4–32.2) mg/kg for verapamil, 0.16 (0.05–0.46) mg/kg for loperamide, and 20.7 (6.0–70.7) mg/kg for 2-(5-diethylaminopent-3-ynyl)-2-(9-hydroxy-9H-xanthen-9-yl)-1,3-dithiane.

What is claimed is:

1. A compound of Formula I or II

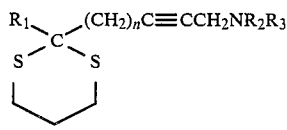

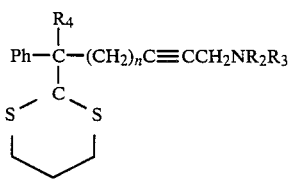

or a pharmaceutically acceptable salt thereof wherein:

$R_1$ is selected from the group consisting of hydrogen, phenyl, 9H-fluoren-9-yl, 10,11-dihydro-5H-dibenzo[a,d]cyclohepten-5-yl, 5H-dibenzo[a,d]cyclohepten-5-yl, 9H-xanthen-9-yl, 9H-thioxanthen-9-yl, 2-chloro-9H-thioxanthen-9-yl, 1,2,3,4-tetrahydro-1-naphthyl, 4H-chromanyl, diphenylmethyl, phenylcycloalkylmethyl, phenylcycloalkylmethyl in each of which the bridgehead methylene is substituted with a hydroxy group, and the foregoing phenyl or benzo-fused rings substituted with one or more $R_5$ groups;

$R_2$ and $R_3$, which may be the same or different, are selected from the group consisting of hydrogen, lower alkyl, phenylalkyl ($C_1$-$C_5$), and phenylalkyl substituted with one or more $R_5$ groups, or $NR_2R_3$ taken together are selected from the group consisting of pyrrolidinyl, piperidinyl, morpholinyl, thiomorpholinyl, 1-piperazinyl and 1-piperazinyl substituted at the 4-position with hydrogen, lower alkyl, hydroxy-substituted lower alkyl, amino-substituted lower alkyl, or acetoxy-substituted lower alkyl;

$R_4$ is hydrogen, hydroxyl or trimethylsilyloxy;

$R_5$ is selected from the group consisting of halogen, trifluoromethyl, lower alkyl, hydroxy and lower alkoxy groups;

Ph is an unsubstituted phenyl group or a phenyl group substituted by one or more $R_5$ groups; and n is 2–4.

2. The compound of claim 1 wherein $R_1$ is selected from 9H-xanthen-9-yl, 9H-thioxanthen-9-yl, 10,11-dihydro-5H-dibenzo[a,d]cyclohepten-5-yl, phenylcycloalkylmethyl and phenylcycloalkylmethyl in which the bridgehead methylene is substituted with a hydroxy group, $R_2$ and $R_3$ are ethyl and n is 2 or 3.

3. A pharmaceutical composition for treatment of irritable bowel syndrome comprising an effective amount of the compound of claim 1 and a pharmaceutically acceptable carrier.

4. A method for treating irritable bowel syndrome comprising administering to a host the composition of claim 3.

* * * * *